(12) United States Patent
Hager et al.

(10) Patent No.: US 7,400,394 B2
(45) Date of Patent: Jul. 15, 2008

(54) CO-DEPLOYED OPTICAL REFERENCING FOR RESPONSIVE DUST-BASED SENSING SYSTEM

(75) Inventors: Harold E. Hager, Bellevue, WA (US); William D. Sherman, Renton, WA (US)

(73) Assignee: The Boeing Company, Chicago, IL (US)

( * ) Notice: Subject to any disclaimer, the term of this patent is extended or adjusted under 35 U.S.C. 154(b) by 254 days.

(21) Appl. No.: 11/131,173

(22) Filed: May 17, 2005

(65) Prior Publication Data

US 2006/0262299 A1    Nov. 23, 2006

(51) Int. Cl.
*G01J 1/10* (2006.01)
(52) U.S. Cl. .................................. 356/243.1
(58) Field of Classification Search ............. 356/243.1, 356/234.1
See application file for complete search history.

(56) References Cited

U.S. PATENT DOCUMENTS

| | | | |
|---|---|---|---|
| 3,831,318 A | | 8/1974 | Richmond |
| 4,102,138 A | | 7/1978 | Dreker et al. |
| 4,121,790 A | | 10/1978 | Graham |
| 4,899,962 A | | 2/1990 | Mueller |
| 5,188,186 A | | 2/1993 | Nash |
| 5,538,781 A | | 7/1996 | Rao et al. |
| 6,383,619 B1 * | | 5/2002 | Engler et al. ................ 428/212 |
| 6,414,735 B1 * | | 7/2002 | Kim et al. .................... 349/113 |
| 6,521,145 B1 * | | 2/2003 | Engler et al. ................. 264/1.9 |
| 6,539,873 B2 * | | 4/2003 | Diller ......................... 102/458 |
| 6,720,936 B1 * | | 4/2004 | Koolish et al. ............... 343/910 |
| 2002/0189485 A1 * | | 12/2002 | Diller ......................... 102/458 |
| 2006/0183579 A1 * | | 8/2006 | Afshari ....................... 473/586 |

OTHER PUBLICATIONS

Johnson, S. G. (2003). Photonic crystals: periodic surprises in electromagnetism. *One-week seminar (five ⅓ hour lectures) MIT MRS Chapter, 2003 IAP tutorial series.* http://ab-initio.mit.edu/photons/tutorial/, (Oct. 6, 2005).
Chemical impact: fireworks., *HM chem general chemistry online.* http://www.hmchemdemo.clt.binghamton.edu/zumdahl/docs/chemistry/07atomstructure/library.../ (Nov. 30, 2004).

(Continued)

*Primary Examiner*—Tarifur R. Chowdhury
*Assistant Examiner*—Isiaka O Akanbi
(74) *Attorney, Agent, or Firm*—Harness, Dickey & Pierce, P.L.C.

(57) ABSTRACT

Apparatus and methods for calibrating an optical detector. In one embodiment an optical reference apparatus includes a body having an outer surface. At least a portion of the outer surface has a reflectance that can vary. The optical reference apparatus is adapted to be deployed with a cloud of optical sensors and has a terminal velocity that is about the same as the terminal velocity of the sensors. Further, the variation of the reflectance can be caused by a rotation of the optical reference apparatus (caused by an aerodynamic member). The sensors may be made from porous silicon and the optical reference apparatus may include a retroreflector. The apparatus also provides a method of referencing an optical signal. The method includes deploying an optical reference apparatus with a cloud of sensors and detecting a variation in its reflectance.

11 Claims, 4 Drawing Sheets

OTHER PUBLICATIONS (Sep. 7, 2004). Pyrotechnics. *Hummel Croton Inc.* http://www.hummelcroton.com/main/pyro.html (Nov. 30, 2004).

Bryden Dr. W. Threat agent cloud tactical intercept & countermeasure (TACTIC). http://www.darpa.gov/spo/programs/tactic.htm (Oct. 29, 2004).

Sailor M. Silicon gets sensitive. Archives special focus section. http://oemagazine.com/fromTheMagazine/mar03/silicon.html (Oct. 29, 2004).

Pavesi L., Mulloni V (2000). Electrochemically oxidised porous silicon microcavities. *Materials science and engineering* B69-70 (2000) 59-65. www.elsevier.com/locate/mseb.

LUU -2 flare. *Global security.* http://www.globalsecurity.org/military/systems/munitions/luu2.htm (Nov. 1, 2004).

LUU-19 flare. *FAS military analysis network.* http://www.fas.org/man/dod-101/sys/dumb/luu19.htm (Nov. 1, 2004).

Li, Y., Cunin, F., Link J., Gao, T., Betts, R., Reiver, S., Chin, V., Bhatia, S., Sailor, M. (2003). Polymer replicas of photonic porous silicon for sensing and drug delivery applications. *Research Articles (Science* vol. 229) . http://www.sciencemag.org (Mar. 28, 2003).

Porous silicon based biosensors. *Faculty of science & engineering school of chemistry, physics & earth sciences.* http://www.scieng.flinders.edu.au/cpes/people/voelcker_n.html_files/biosensors.html. (Feb. 2, 2006).

Airbags may bounce back to mars (2000). *Red planet rebound—airbags to cushion mars landing.* http://www.space.com/scienceastronomy/solarsystem/mars_airbags_000707.html (Mar. 1, 2006).

Liquid body armor in the works (2004). *CBS news scitech.* http://www.cbsnews.com/stories/2004/04/30/tech/main614961.shtml (Jan. 24, 2005).

Swarts, D. (2002). How airfence works. *Roadracing world action fund roadracing & motorcycle technology.* http://actionfund.roadracingworld.com/News/Article/?ARTICLE_ID=191 (Feb. 6, 2006).

Temporary water-inflated portable dams for construction worksite dewatering reusable cofferdams, flood control products and flood barriers. *Aqua-Barriers water-inflated dams.* http://www.aquabarrier.com/ (Feb. 6, 2006).

USCD researchers fabricate tiny "smart dust" particles capable of detecting bioterrorist and chemical agents. *University of California, San Diego science & engineering press release.* http://ucsdnews.ucsd.edu/newsrel/science/mcsmartdust.htm (Feb. 6, 2006).

Targeted smart dust how it works. *UCSD Sailor Research Group, University of California, San Diego department of chemistry and biochemistry.* http://chem-faculty.ucsd.edu/sailor/research/smartdust.htm (Feb. 6, 2006).

* cited by examiner

CO-DEPLOYED OPTICAL REFERENCING FOR RESPONSIVE DUST-BASED SENSING SYSTEM This application is related to and incorporates by reference U.S. patent application Ser. No. 11/131,171, entitled Enhanced Signal Detection of Optically Encoded Particles via Flare, and filed by Koshinz on May 17, 2005.

FIELD

This disclosure relates generally to apparatus and methods for calibrating optical detectors, and, more particularly, apparatus and methods for calibrating remote optic detectors used in conjunction with a cloud of porous silicon optical sensors to detect airborne chemicals.

BACKGROUND

Clouds of pollution and other airborne materials are difficult to detect. Yet the concentration of these materials needs to be measured to enable those near the cloud to respond in an appropriate manner. Without an accurate assessment of the strength of the cloud unnecessary evacuations may be ordered or a needed evacuation may not be deemed necessary. The materials that can occur in these clouds include man-made pollution (e.g. a release from a chemical plant), natural pollution (e.g. volcanic fumes), and chemical and biological warfare agents. The difficulty of detecting these clouds arise for several reasons. First, the materials may be invisible and otherwise undetectable by human beings even at concentration levels that pose an immediate health threat. Second, the clouds tend to move with the wind so that, once released, they can travel long distances, thereby appearing without warning. Further, drafts, inversions, and other thermal gradients can cause the cloud to concentrate in some geographic areas (e.g. valleys) while dispersing rapidly from other areas (e.g. hilltops). Similarly, the cloud might be found at some altitudes and not found at others. Also, because these clouds might be found at some height above the ground, it may not be possible to place an instrument in the cloud short of flying a probe into the cloud. The clouds may also have irregular shapes with ill-defined boundaries (i.e. the cloud boundary may be marked by either a sharp or gradual concentration gradient or some combination of the two). Thus, where a particular cloud might be found is subject to a number of vagaries that cause difficulties in predicting where the cloud might exist.

One solution to these problems is to deploy a cloud of minute optical sensors into the suspected location(s) of the clouds. These clouds of minute sensors are sometimes referred to as responsive or "smart dust." Recently, porous silicon optical sensors have become available for this application. Each of these sensors is manufactured from silicon that has been etched to create a porous surface. The etching process is tailored to create pores of a size, depth and number to enable the sensors to selectively bind to a particular, preselected material. When the sensors encounter that particular material, the material reacts with the silicon of the sensor. By various mechanisms that depend on the particular material involved, the reflectance spectrum of the silicon changes as a result of the reaction. Thus, observing the reflectance spectrum of the sensors yields a measure of the amount of the material that the sensors have encountered.

In practice, an intense electromagnetic energy source (e.g. a laser or an equivalent) illuminates the sensors so that the reflectance spectrum of the sensors can be observed. However, this practice suffers from several problems also. First, the electromagnetic energy ("light") source and the detector that is used to measure the reflectance spectrum must be initially aligned and held in strict alignment during the measurement process. Maintaining the alignment can be quite difficult because, at times, either the source, sensor cloud, or detector will move relative to one and other. Also, environmental factors along the path that the light travels from the source, to the sensors, and then to the detector may cause an attenuation of the light at some of the frequencies that the sensor attenuates reflected light. As a result, when the light arrives at the detector from the sensor, it is difficult to ascertain whether the attenuation of the light was caused by the sensor's exposure to the material or due to the environmental factors.

SUMMARY

In a first embodiment, the present disclosure provides a co-deploy optically oscillating mirror device as part of a warfare agent responsive dust (WARD) system. The convex reference mirror device (RMD) incorporates structures (e.g., fins or rotors) that induce rotation of the RMD as it falls with the WARD. The RMD mass density and aerodynamic drag are designed to produce similar rates-of-fall for the RMDs and the WARD particles. The RMDs incorporate alternating regions of high optical reflectivity and high optical absorption, over the entire spectral range of interest for the WARD measurement. For cases when the collection optics employ an adjacent laser for the illuminating source, retroreflectors give a very high gain reference signal. Alternative embodiments provide optical references that employ actively controlled reflectance. In one embodiment, devices are provided that are designed to optically oscillate between a low and a high reflectivity value employing electro-optic materials in an optically or electronically controlled structure. These active devices may be powered by the optical illumination source, or by batteries on the reference.

In a second embodiment, the present disclosure provides a reference that includes a body and a surface of the body. At least a portion of the surface has a reflectance that can vary. The reference is adapted to be deployed with a cloud of optical sensors and has a terminal velocity (or buoyancy in air) that is about the same as the terminal velocity of the sensors. Further, the variation of the reflectance can be caused by a rotation of the reference (caused by an aerodynamic member) or by a controller that controls an electro optic material of the surface. In one embodiment, the sensors are porous silicon optical sensors and the reference includes a retroreflector. The disclosure also provides a method of referencing an optical signal that includes deploying a reference with a cloud of sensors and detecting a variation in its reflectance.

A third embodiment provides an optical reference that includes a body, a surface of the body, and an aerodynamic member. The body defines an axis of rotation about which the aerodynamic member (e.g. a fin or rotor) causes the reference to rotate. The surface of the body is spaced apart from the axis of rotation and has two portions (e.g. halves) with different reflectances. Preferably, one surface portion has a reflectance between about 80% and about 98% over a spectral range of 400 to 1550 nanometers while the other surface portion has a reflectance between about 5% and about 10%. In the alternative, one of the surface portions can include an electro optic material, the reflectance of which is controlled by a controller and powered by a power supply of the reference. Further, the reference can be adapted to be deployed with a plurality of porous silicon sensors by, for example, having a terminal velocity that is about the same as that of the sensors. Preferably, the surface is convex and includes a retroreflector.

In a fourth embodiment, the present disclosure provides an optical reference. Again, the reference has a body with a surface. In the current embodiment, a portion of the surface has a variable reflectance that is controlled by a controller. Preferably, the variable reflectance is provided by an electro optic material.

Another embodiment of the present disclosure provides a system for detecting airborne contaminants. The system includes an illumination source, a detector, a plurality of optical sensors, and at least one optical reference. The optical sensors are adapted to be deployed as a cloud of sensors that the illumination source illuminates. Further, the detector detects the cloud of sensors and a varying reflectance of the reference. Also, the terminal velocities of the sensors and the reference can be about the same.

In yet another embodiment the present disclosure provides a method of referencing an optical signal. The method of the current embodiment includes deploying an optical reference with a cloud of optical sensors in such a manner that the reference drifts with the cloud of sensors. A reflectance of a surface of the reference is varied. Also, the surface of the reference is illuminated with electromagnetic energy in such a manner that at least a portion of the energy reflects from the surface. Using the reflected portion of the energy, the variation of the reflectance is detected and an attenuation of the reflected energy is determined. Preferably, the variation of the reflectance is caused by either rotating the reference (via, for example, using an aerodynamic member to cause the rotation) or controlling an electro optic material. Moreover, the reference and the sensors can be selected so that their terminal velocities are about the same.

Still another embodiment provides an apparatus for use in detecting an airborne material. The apparatus of the current embodiment includes a container, a plurality of optical sensors, and at least one optical reference. The sensors and the reference are adapted to be deployed from the container as a cloud and to fall at about the same terminal velocity. Again, the reference includes a body with a surface. At least a portion of the surface has a reflectance that varies. Preferably, the container is an artillery shell.

Further features and advantages of the present disclosure, as well as the structure and operation of various embodiments of the present disclosure, are described with reference to the accompanying drawings.

BRIEF DESCRIPTION OF THE DRAWINGS

The accompanying drawings, which are incorporated in and form a part of the specification, illustrate exemplary embodiments of the present disclosure and together with the description, serve to explain the principles of the disclosure. In the drawings.

DETAILED DESCRIPTION

Figure 1:
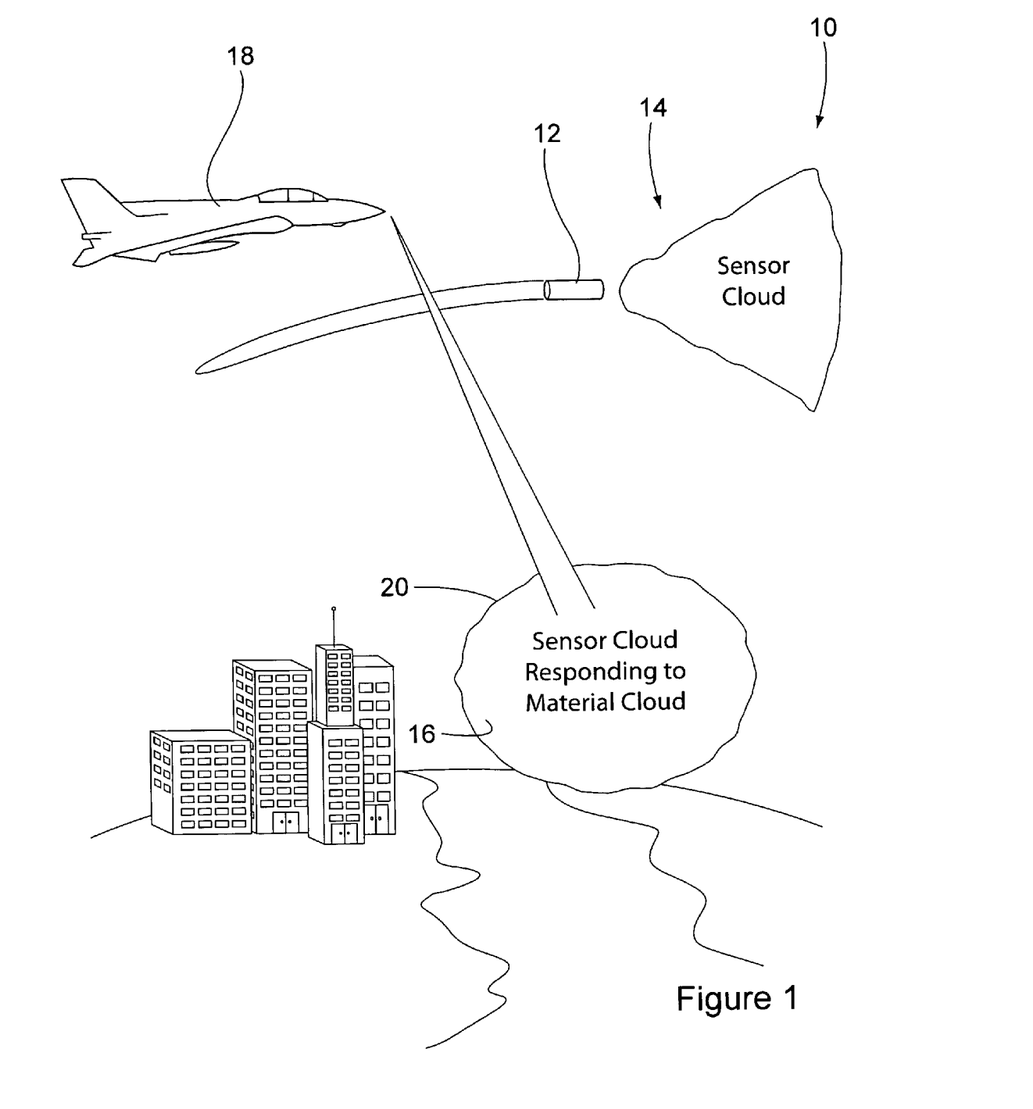
FIG. 1 illustrates an airborne material measuring system constructed in accordance with the principles of the present disclosure.

Referring to the accompanying drawings in which like reference numbers indicate like elements, FIG. 1 illustrates a system 10 constructed in accordance with the principles of the present disclosure.

The system 10 of FIG. 1 includes a deployment mechanism, two clouds 14 and 16 of optical sensors, and a vehicle 18 that includes an optical detector. Also, FIG. 1 shows a cloud 20 of airborne material that can be, for example, a pollutant, a chemical or biological agent, or other impurity in the air. The cloud 16 of sensors is shown, at least partly, as being coincident with the cloud of material 20 whereas the cloud 14 of sensors is shown being spaced apart from the cloud 20. Where the sensors of the cloud 16 are in contact with the material cloud 20 the material reacts with the porous silicon of the sensors and causes the sensors to reflect a different spectrum than the spectrum reflected by the sensors in the unaffected sensor cloud 14.

In operation, deployment mechanisms 12 are positioned to deploy the cloud of sensors 14 and 16 at locations where a cloud 20 of material may be present. The deployment mechanisms then deploy the sensors as the clouds 14 and 16. Where the deployment mechanism 12 is an artillery shell (as shown), a fuse ignites a small charge of explosive material that propels the sensors from the shell to form the cloud 14 or 16. If the material cloud 20 is present where the sensors drift, the sensors react with the material and begin reflecting the altered spectrum (i.e. the sensors change color). The detector onboard the vehicle 18 is then pointed toward the clouds 14 and 16 of sensors to detect, and preferably record, the reflected spectrum. Since the amount of attenuation is related to the concentration of material in the cloud 20, the system 10 measures the concentration of the cloud 20. Preferably, the sensor clouds 14 and 16 are clouds of "smart" or responsive dust.

As discussed in J. R. Link, and M. J. Sailor, Proc. Nat Acad. Sci. 2003 100, 10607-10610 (see also http://chem-faculty.ucsd.edu/sailor/research/smartdust.html), "smart dust" is prepared in a two-step process. In the first step, a porous photonic structure is produced by etching silicon with an electrochemical machining process. This step imparts a highly reflective and specific color-code to the material, that acts like an address, or identifying bar-code for the particles. The second step involves chemically modifying the porous silicon photonic structure so that it will find and stick to the desired target material. The two steps (etch and modify) are repeated with a different color and a different chemistry, yielding films having one side with one color (e.g., red) and the other side with another color (e.g., green). The films are broken up into particles about the size of a human hair and then deployed. Once deployed, the particles seek out and attach themselves to particles or droplets of the target material, presenting one surface (e.g., the red surface) to the outside world and the other (e.g., green) surface towards the inside of the particle or droplet.

Once they find the material for which they were programmed, the individual optical sensors (i.e., the smart dust particles) begin to line up, or "tile" themselves on the surface of the target droplet. The optical properties of the tiled particle combine to give a mirror whose characteristic color is easily observed. This collective behavior provides a means of amplifying the molecular recognition event that occurs at the surface of each individual target particle. As a means of signaling their presence at the target droplet, the smart dust particles (i.e., nanostructure) change color in a predictable fashion. As the nanostructure comes in contact with the target material, 
some of the liquid from the target material is absorbed into it. The liquid wicks into the regions of the nanostructure that have been modified with the appropriate chemistry. Thus, the presence of the target material in the nanostructure causes a predictable change in the color code, signaling to the outside observer that the correct target material has been located.

Figure 2:
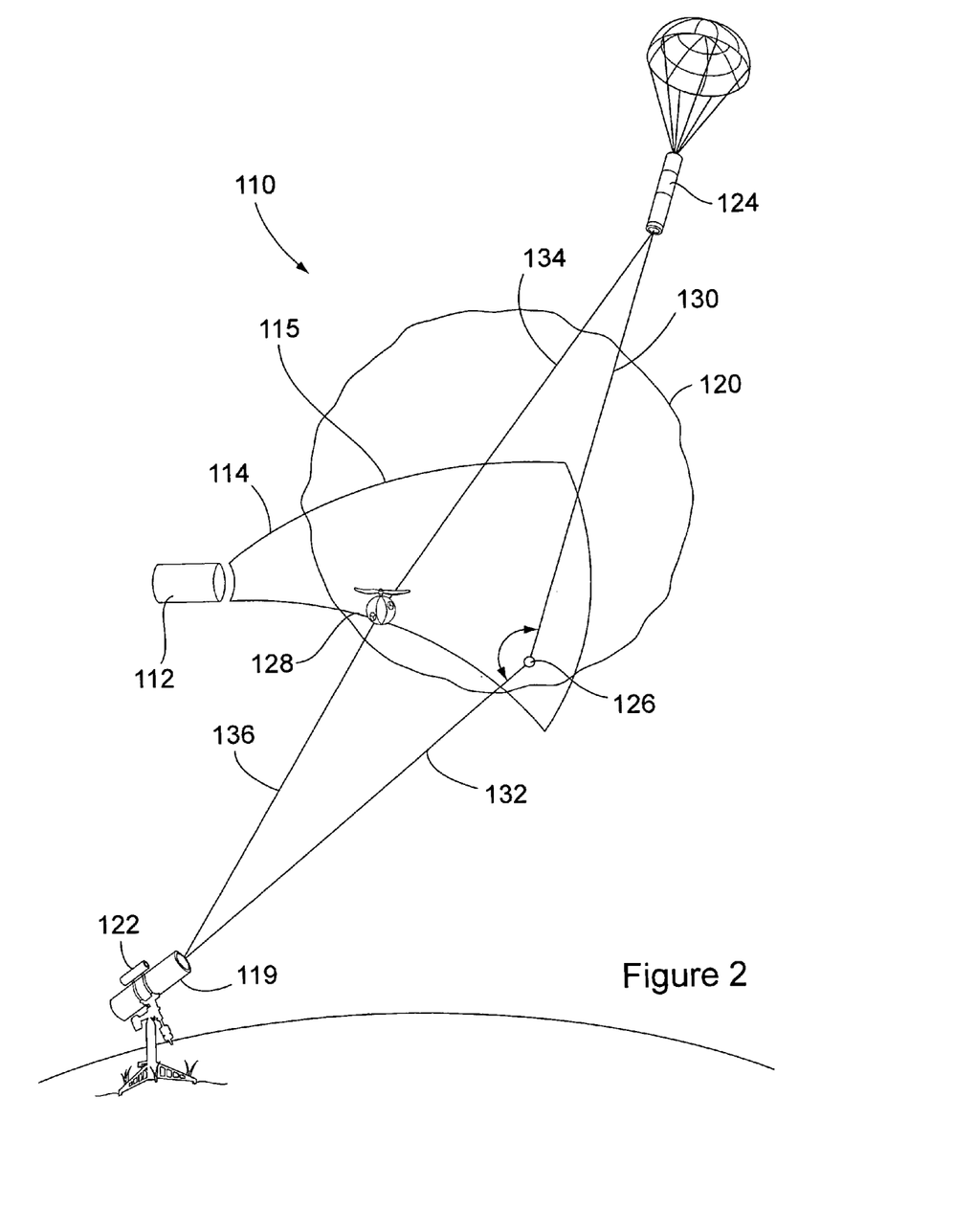
FIG. 2 illustrates a system of an embodiment of the present disclosure.
Figure 3:
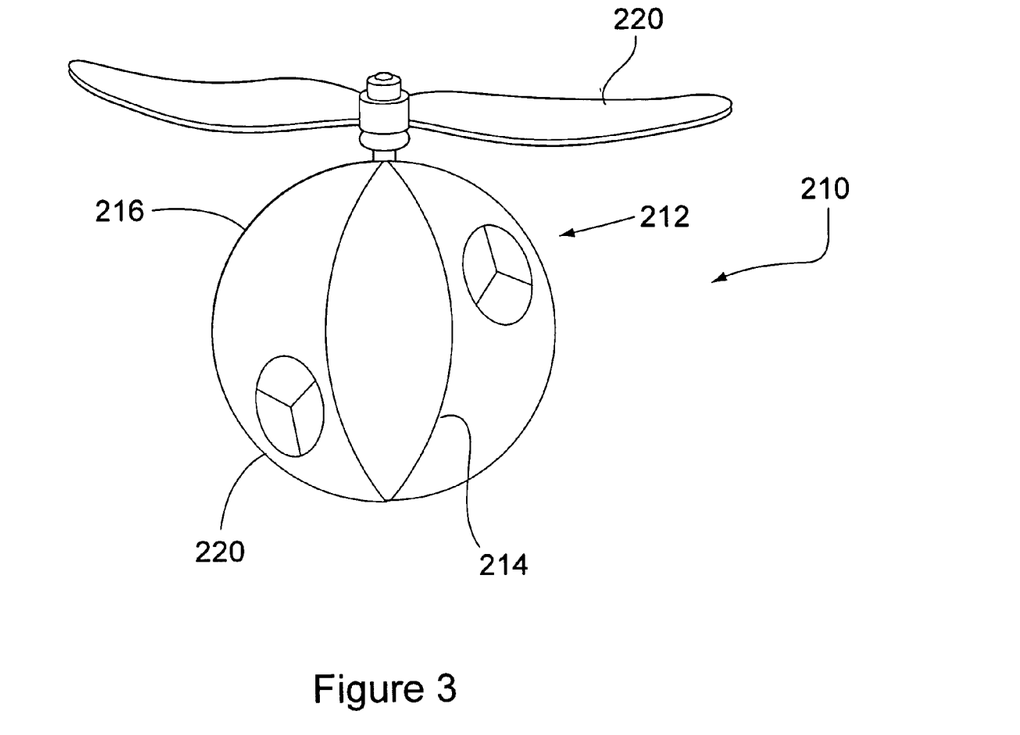
FIG. 3 illustrates an optical reference of another embodiment.
Figure 4:
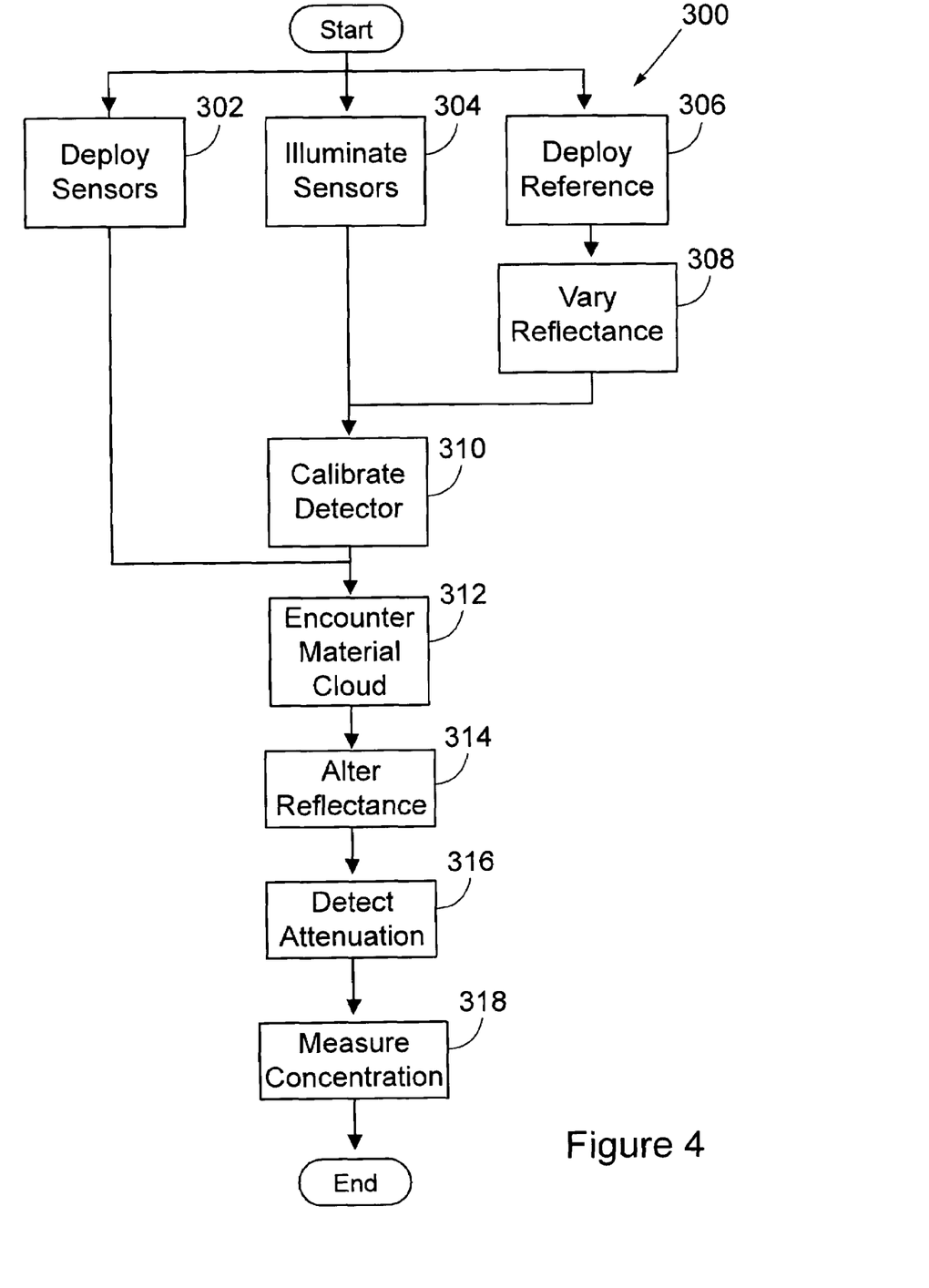
FIG. 4 illustrates another optical reference of another embodiment.

In a embodiment, these nano-structured "smart dust" chemical (or biological agent) sensors use no power, are the size of dust particles, and can be probed at a remote distance using visible or infrared laser technology. Nano-scale holes in the porous silicon matrix act as concentrators, condensing vapors of the analyte. Catalytic reactions take place in small micellar nano-reactors in the porous silicon, converting the target material (if present in the analyte) into a chemical that can be recognized specifically by the matrix, thereby causing a signal that scales with dose in the from of a predictable color change. For additional information the reader is referred to T. A. Schmedake, F. Cunin, J. R. Link, and M. J. Sailor, Adv. Mater. 2002, 14, 1270-1272, and J. Am. Chem. Soc. 2000, (22), 5399-5400), and University of California, San Diego, "UCSD RESEARCHERS FABRICATE TINY 'SMART DUST' PARTICLES CAPABLE OF DETECTING BIOTERRORIST AND CHEMICAL AGENTS," Sep. 2, 2002-Viewed Online Feb. 8, 2005 at http://ucsdnews.ucsd.edu/newsrel/science/mcsmartdust.htm, for additional information.

Turning now to FIG. 2, another exemplary system 110 that is provided by the present disclosure is illustrated. The system 110 differs from the system 10 of FIG. 1 in that FIG. 2 shows only one cloud 114 of sensors including a portion 115 that overlaps the material cloud 120. FIG. 2 also shows a detector 119, two illumination sources 122 and 124, an individual sensor 126, an optical reference apparatus 128, and the paths 130, 132, 134, and 136 between the components of the system 110. The detector 119 can be any device capable of detecting the reflectance spectrum of the sensor 126 and is, preferably, a charge coupled device (CCD) having infrared, near infrared, and visible detection capabilities. The source 122 can be a laser (or its equivalents). Further, the source 122 is aligned with the detector 119 and sensor 126 so that the source 122 directs electromagnetic energy (across an appropriate range of wavelengths) toward the sensor 126 where the electromagnetic energy is reflected toward the detector 119. In a one embodiment the other illumination source 124 is an aerial flare with a retarding parachute to prolong its descent through the air. Either illumination source 122 or 124, or both, can be used. The sensor 126 can be a porous silicon sensor with a porosity tailored for sensitivity to a pre-selected material. Thus, the reflectance of the sensor 126 varies depending on the presence of the material at the sensor 126. In contrast, the optical reference apparatus 128 has a reflectance that varies in a pre-selected manner (e.g. oscillates) between a high value and a low value.

Light from the illumination source 124 (which may be a flare) illuminates the volume of air (an "area") that is suspected of containing the material cloud 120. Because the sensor cloud 114 has been deployed in that vicinity, light travels along path 130 from the illumination source 124 to at least some of the particles of this sensor 126. Depending on the concentration of material sensed by the sensor 126, the light is attenuated by an amount at predictable wavelengths by the sensor 126. The attenuated light from at least some particles of the illuminated sensor 126 then travels along the path 132 to the detector 119 where the concentration is detected remotely.

Theoretically, it is possible to detect the material cloud 120 from a great distance. However, attenuation and scattering of the light along the paths 130 and 132 may alter the light arriving at the detector 119. Further, it is possible that the attenuation (along the paths 130 and 132) of the light may be at those wavelengths affected by the sensor's 126 contact with the material of the cloud 120. Thus, it will be unclear whether the attenuation of the light as it arrives at the detector 119 is due to the sensor 126 or environmental factors along the paths 130 and 132. Accordingly, the disclosure provides the optical reference apparatus 128 that can be co-deployed with the sensor cloud 120.

As noted above, the reflectance of the optical reference apparatus 128 varies with time between a high value and a low value across the entire range of active wavelengths for the apparatus 128 sensor. As shown, the optical reference apparatus 128 is deployed to a location within, or near, the sensor cloud 114 and is adapted to generally remain with the cloud 114 as the cloud 114 drifts with wind (including up and down drafts) and under the influence of gravity. Thus, the path 134 between the illumination source 124 and the optical reference apparatus 128 and, from there, the path 136 to the detector 119 are immediately adjacent to the paths 130 and 132, respectively, associated with the sensor 126. As a result, the environmental factors along the paths 130 and 132 are quite similar to the factors along the paths 134 and 136. Therefore the attenuation along these sets of paths will be essentially the same.

Thus, identifying the light reflected from the optical reference apparatus 128 enables the measurement and correction for the environmentally induced attenuation of the light along the paths 130 and 132. According to the principles of the present disclosure, the reflectance of the optical reference apparatus 128 is therefore varied to provide an easily recognizable signal to identify the apparatus 128 to the detector 119. Preferably, the reflectance oscillates between a high value of about 90% and a low value of about 10%. Moreover, because the reflectance will vary in a pre-selected manner, the detector 119 can be programmed, or otherwise adapted, to detect the varying reflectance signal from the optical reference apparatus 128. By comparing the attenuation of the light arriving from the optical reference apparatus 128 when the light is at its maximum and at its minimum, the detector 119 identifies and measures the amount of environmentally induced attenuation that affects the light arriving from both the optical reference apparatus 128 and the sensor 126. Subtracting the environmental attenuation from the attenuation of the light arriving from the paths 130 and 132 therefore yields the attenuation due to the sensor 126 (due to the concentration of the material in the cloud 120). Thus, the system 110 remotely measures the concentration of the cloud 120.

With reference now to FIGS. 3 and 4, an optical reference apparatus 210 of one embodiment of the present disclosure is shown. The optical reference apparatus 210 includes a body 212, two portions 214 and 216 of the surface of the body 212, and an aerodynamic member 220. The body 212 is shown as a sphere although it could be any number of shapes with preferably convex sides. The aerodynamic member 220 is preferably a fin or rotor attached to the body 212 at the top. The surface portion 214 has a low reflectance (preferably about 5%) while the surface portion 216 has a high reflectance (preferably about 95%). The reflectances of the surface portions 214 and 216 are further over a range of about 400 nanometers to about 1550 nanometers. Further, the surface portions 214 and 216 correspond to hemispheres of the spherical body 212 with the rotor 220 connecting to the body 212 at a pole of the sphere. As the optical reference apparatus 210 falls through the air, the rotor 220 causes the body 212 to rotate. Thus, the surface portions 214 and 216 are presented to any direction about the optical reference apparatus 210 in an alternating fashion. Accordingly, the detector 119 (see FIG. 2) sees a reflection from the optical reference apparatus 210 that alternates in a sinusoidal fashion between high and low according to the differing reflectances of the surface portions 214 and 216 as they rotate about the axis of rotation of the body 212. In other words, the surface portions 214 and 216 are defined by a plane 217 (FIG. 4) through the spherical body 212 with the axis of rotation of the body 212 lying in that plane 217. In another embodiment, the surface of the body 212 consists of a large number (e.g., 1000) of pixels. Every other pixel is treated to have either a high reflectance or low reflectance with the remaining pixels having the other reflectance. Thus, half of the surface has one reflectance and the other half of the surface as the other reflectance.

In another embodiment the rotor 220 is made from or coated with a material having a low reflectance (e.g. 5%). In contrast, the high reflectance surface portion 216 is coated with, contains, or is the surface of a retroreflector so that light incident on the reflective surface portion 216 is reflected to the maximum extent possible and in the direction from which it came. Thus, the current embodiment maximizes the difference between the amount of light reflected to the detector 119 when the high reflectance portion 216 is presented to the detector 119 and the amount of light reflected when the low reflectance portion 214 is presented to the detector 119.

Figure 5:
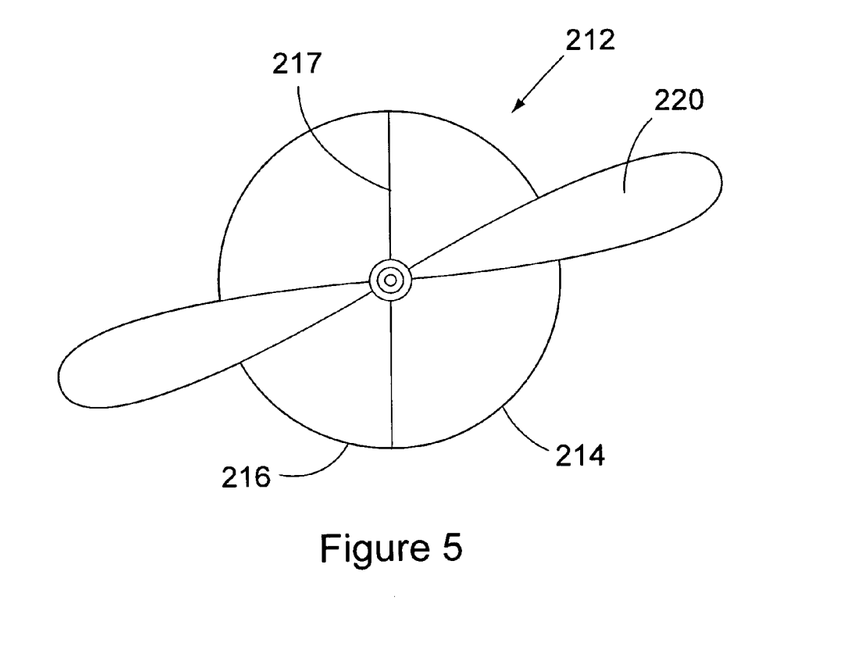
FIG. 5 illustrates a method in accordance with the principles of the present disclosure.

Turning now to FIG. 5, and exemplary method 300 in accordance with the principles of the present disclosure is illustrated. The method of the current embodiment generally includes deploying the sensors and reference(s), calibrating the detector, and measuring the concentration of the material in an airborne cloud. More particularly, the method 300 includes deploying a cloud of optical sensors in operation 302. The sensors may be porous silicon optical sensors deployed from an artillery shell, unmanned aerial vehicle, manned aircraft or other mobile platform. More particularly, the deployment usually occurs in an area prone to, or suspected of, experiencing the presence of an airborne cloud of material. An illumination source (e.g. a flare or laser) is positioned to illuminate the cloud of sensors, If need be, depending on the type of detector and illumination source used, it may be desirable to align the various components of the system. See operation 304. At some time, the optical reference apparatus (128 or 210) is also deployed as illustrated at operation 306. Preferably, the optical reference apparatus is deployed with the cloud of sensors and is adapted to remain with the sensors.

The reflectance of the optical reference apparatus is then varied as in operation 308. The variation can be pre-selected so that the detector 119 can readily identify the pattern caused by the variation. In one embodiment the reflectance variation is a sinusoidal oscillation between a pre-selected maxima and a pre-selected minima although many other patterns can be employed. With the reflectance of the optical reference apparatus varying, the detector 119 is then pointed toward, or otherwise allowed to view, the cloud of sensors. Without the optical reference apparatus being present, the detector 119 would view the cloud of sensors (some reflecting radiation attenuated by the interaction of the sensors and the material of the cloud, some reflected the radiation without appreciable attenuation). Also, the detector 119 will typically view background radiation that may be at, or near, the wavelengths that the sensors attenuated in the presence of the material cloud. More particularly, during daylight operations, the background radiation may be intense enough to make detecting the wanted attenuation (that attenuation caused by the presence of the material) difficult. Because the pattern of the reflectance variation is known, the detector 119 can readily identify the optical reference apparatus against this potentially cluttered background.

In particular, the preferred sinusoidal variation is readily identifiable. Thus, the detector 119 can be programmed (or otherwise adapted) to identify the variation, and determine from a comparison of the optical reference apparatus signal's maxima and minima amplitude (i.e. brightness) at the wavelengths of interest, the amount of attenuation occurring along the path from the source, to the optical reference apparatus, and to then to the detector. Thus, the signal from the optical reference signal allows the detector to be calibrated even in the presence of environmental influences. See operation 310.

At some time, the sensor cloud (with the optical reference apparatus 128 or 210 therein) will encounter a cloud of the material for which the sensor cloud has been tailored to detect. Accordingly, the material will react with the sensor cloud and cause a change in the reflectance spectrum of the sensor cloud. See operations 312 and 314. With the sensors reflecting spectra according to the presence, or lack thereof, of the material, the reflected spectra are detected as illustrated in operation 316. A comparison between the maxima of the reference signal and the signal reflected (and attenuated) by the sensor cloud therefore measures the concentration of the material in the sensor cloud. See operation 318.

With the system and method of the present disclosure, the airborne material measuring system requires no alignment between the illumination source and detector. Furthermore, the various embodiments of the system can be calibrated in real-time, and continuously, as long as an optical reference apparatus is in, or near, the sensor cloud. Moreover, the various embodiments of optical reference apparatuses provided by the present disclosure can be deployed with, and drift with, the cloud of sensors until the cloud (including the reference) settles on the ground or other surface. Even after settling, the optical reference apparatus can continue varying its reflectance (particularly for the embodiments that include an electro-optical material) so that the detector can detect the optical reference apparatus and the optical changes in the sensors.

The described embodiments were chosen to explain the principles of the invention and its practical application to enable those skilled in the art to use the invention in various embodiments and with various modifications as are suited to the particular use contemplated.

As various modifications could be made in the constructions and methods described and illustrated without departing from the scope of the invention, the description should be interpreted as illustrative rather than limiting. Thus, the breadth and scope of the present invention should not be limited by any of the exemplary embodiments, but should be defined only in accordance with the claims.

What is claimed is:

1. An optical reference apparatus for use in calibrating an optical detector used in an optical detection system, the optical reference apparatus comprising:

a body having an outer surface; and at least a portion of the outer surface having a reflectance that varies, the optical reference device adapted to be deployed in a cloud of optical sensors, the optical sensors having a first buoyancy, the optical reference apparatus having a second buoyancy that is approximately the same as the first buoyancy, such that the optical reference apparatus tends to drift with said optical sensors while said optical sensor apparatus is being optically imaged by said detector.

2. The optical reference apparatus according to claim 1, further comprising an aerodynamic member adapted to cause the optical reference apparatus to rotate as the optical reference apparatus falls, the rotation causing the variation of the reflectance as perceived by said detector.

3. An optical reference apparatus comprising:
- a body defining an axis of rotation;
- a surface of the body;
- a first portion of the surface having a first reflectance and being spaced apart from the axis of rotation;
- a second portion of the surface, the first portion having a second reflectance that is different than the first reflectance and being spaced apart from the axis of rotation; and
- an aerodynamic member coupled to the body, the member adapted to cause the body to rotate about the axis of rotation;
- wherein the optical reference apparatus is adapted to be deployed with a plurality of porous silicon sensors, each sensor having a first buoyancy, the optical reference apparatus having a second buoyancy that is approximately the same as the first buoyancy.

4. A system for detecting airborne contaminants, the system comprising:
- an illumination source;
- a detector;
- a plurality of optical sensors adapted to be deployed as a cloud of sensors, the illumination source to illuminate the cloud of sensors, the detector to detect the cloud of sensors; and
- at least one optical reference adapted to be deployed with the cloud of sensors, the optical reference including a body and a surface of the body, at least a portion of the surface having a varying reflectance, the detector to detect the varying reflectance.

5. The system according to claim 4, wherein the sensors are porous silicon sensors.

6. The system according to claim 4, wherein each of the sensors has a first buoyancy, the reference having a second buoyancy that is approximately the same as the first buoyancy.

7. The system according to claim 4, wherein the illumination source is adapted to further illuminate the cloud of sensors with electromagnetic energy having a wavelength of about 400 nanometers to about 1550 nanometers.

8. A method of referencing an optical signal, the method comprising:
- deploying an optical reference apparatus with a cloud of optical sensors in such a manner that the optical reference apparatus drifts with the cloud of sensors;
- varying a reflectance of a surface of the optical reference apparatus;
- illuminating a surface of the optical reference apparatus and the cloud of sensors with electromagnetic energy in such a manner that at least a portion of the electromagnetic energy reflects from the surface of the optical reference apparatus and from the cloud of sensors;
- detecting the variation of the reflectivity using the reflected portion of the electromagnetic energy from the optical reference apparatus;
- determining an attenuation of the electromagnetic energy from the reflected portion of the electromagnetic energy; and
- using the attenuation to assist in determining an accuracy of reflected electromagnetic energy from said cloud of sensors.

9. The method according to claim 8, the varying including rotating the reference.

10. The method according to claim 9, the rotating further comprising being caused by an aerodynamic force on the reference.

11. The method according to claim 8, further comprising selecting the reference in such a manner that the reference has a buoyancy approximately the same as a buoyancy of the sensors.

\* \* \* \* \*